US 11,284,779 B2

(12) United States Patent
Fujisawa (10) Patent No.: US 11,284,779 B2
(45) Date of Patent: Mar. 29, 2022

(54) ENDOSCOPE

(71) Applicant: OLYMPUS CORPORATION, Tokyo (JP)

(72) Inventor: Yutaka Fujisawa, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 17/119,280

(22) Filed: Dec. 11, 2020

(65) Prior Publication Data

US 2021/0093167 A1 Apr. 1, 2021

Related U.S. Application Data

(63) Continuation of application No. PCT/JP2019/008053, filed on Mar. 1, 2019.

(30) Foreign Application Priority Data

Jun. 26, 2018 (JP) .............................. JP2018-120972

(51) Int. Cl.
*A61B 1/00* (2006.01)
*A61B 1/045* (2006.01)
(Continued)

(52) U.S. Cl.
CPC ...... *A61B 1/00114* (2013.01); *A61B 1/00009* (2013.01); *A61B 1/00124* (2013.01);
(Continued)

(58) Field of Classification Search
CPC ............ A61B 1/00006; A61B 1/00009; A61B 1/00018; A61B 1/00096; A61B 1/00114;
(Continued)

(56) References Cited

U.S. PATENT DOCUMENTS 4,488,039 A * 12/1984 Sato ................... A61B 1/00188
250/216
5,876,327 A * 3/1999 Tsuyuki ............. A61B 1/00188
600/112
(Continued)

FOREIGN PATENT DOCUMENTS

| JP | 11-047091 A | 2/1999 |
|---|---|---|
| JP | 2009-279148 A | 12/2009 |
| JP | 2011-036585 A | 2/2011 |

OTHER PUBLICATIONS

International Search Report dated May 28, 2019 received in PCT/JP2019/008053.

*Primary Examiner* — Peter D Le
(74) *Attorney, Agent, or Firm* — Scully, Scott, Murphy & Presser, P.C.

(57) ABSTRACT

An endoscope includes: an insertion portion to be inserted into a subject; a distal end portion that is arranged on a distal end side of the insertion portion, the distal end portion including as imager and an actuator; an operating portion that is arranged on a proximal end side of the insertion portion, the operating portion including a relay substrate that is electrically connected to the imager and the actuator via a first cable; a connector substrate that is electrically connected to the relay substrate via a second cable; and a proximal end portion including a connector. The first cable includes a first actuator signal line. The second cable includes a second actuator signal line. The second actuator signal line has a larger outer diameter than an outer diameter of the first actuator signal line.

7 Claims, 6 Drawing Sheets

(51) Int. Cl.
  *A61B 1/05*    (2006.01)
  *H04N 5/225*   (2006.01)
  *H04N 5/232*   (2006.01)
  *H04N 7/18*    (2006.01)

(52) U.S. Cl.
  CPC ............... *A61B 1/045* (2013.01); *A61B 1/05* (2013.01); *H04N 5/2253* (2013.01); *H04N 5/23216* (2013.01); *H04N 7/183* (2013.01); *H04N 2005/2255* (2013.01)

(58) Field of Classification Search
  CPC . A61B 1/00124; A61B 1/00188; A61B 1/045; A61B 1/05; G02B 23/24; H04N 2005/2255; H04N 5/2253; H04N 5/23216; H04N 7/181; H04N 7/183
  See application file for complete search history.

(56) References Cited

U.S. PATENT DOCUMENTS

| | | | | |
|---|---|---|---|---|
| 6,104,426 A | * | 8/2000 | Street | G02B 23/2415 348/45 |
| 6,154,315 A | * | 11/2000 | Street | A61B 1/00193 348/45 |
| 6,222,996 B1 | * | 4/2001 | Nonaka | G02B 7/32 396/104 |
| 6,970,189 B1 | * | 11/2005 | Bernstein | H04N 5/23225 348/211.2 |
| 10,441,145 B2 | * | 10/2019 | Kugimiya | A61B 1/045 |
| 2002/0161279 A1 | * | 10/2002 | Luloh | G02B 7/08 600/112 |
| 2002/0161280 A1 | * | 10/2002 | Chatenever | A61B 1/042 600/112 |
| 2005/0143664 A1 | * | 6/2005 | Chen | A61B 5/6852 600/478 |
| 2009/0185032 A1 | * | 7/2009 | Sakai | A61B 1/00096 348/65 |
| 2009/0225156 A1 | * | 9/2009 | Akiyama | A61B 1/00096 348/68 |
| 2009/0253966 A1 | * | 10/2009 | Ichimura | A61B 1/12 600/175 |
| 2009/0287047 A1 | * | 11/2009 | Onoda | A61B 5/06 600/109 |
| 2010/0141828 A1 | * | 6/2010 | Higuchi | G03B 13/00 348/349 |

* cited by examiner

ENDOSCOPE

CROSS-REFERENCE TO RELATED APPLICATIONS

This application is a continuation of PCT international application No. PCT/JP2019/008053 filed on Mar. 1, 2019, which designates the United States, incorporated herein by reference, and which claims the benefit of priority from Japanese Patent Application No. 2018-120972, filed on Jun. 26, 2018, incorporated herein by reference.

BACKGROUND

1. Technical Field

The present disclosure relates to an endoscope that captures an image of an object and generates image data of the object.

2. Description of the Related Art

In the related art, in an endoscope, an imaging element is arranged inside a distal end portion of an insertion portion to be inserted into a subject, and electric power is supplied from a video processor to the imaging element via an electrical cable (see Japanese Laid-open Patent Publication No. 2009-279148). In this technology, a frame member is an operating portion that is connected to a proximal end portion of the insertion portion electrically connect the insertion portion and a shield of the electrical cable in order to reduce a diameter of the electrical cable.

SUMMARY

In some embodiments, an endoscope includes: an insertion portion to be inserted into a subject; a distal end portion that is arranged on a distal end side of the insertion portion, the distal end portion including an imager and as actuator, the imager being configured to adjust a focal point and generate an imaging signal by capturing an image of an object, the actuator being configured to adjust a focal point of the imager based on a driving signal that is input from outside; an operating portion that is arranged on a proximal end side of the insertion portion, the operating portion including a relay substrate that is electrically connected to the imager and the actuator via a first cable; a connector substrate that is electrically connected to the relay substrate via a second cable; and a proximal end portion including a connector configured to receive input of the driving signal from a processing device and output the imaging signal to the processing device. The first cable includes a first actuator signal line that transmits the driving signal from the relay substrate to the actuator, the second cable includes a second actuator signal line that transmits the driving signal from the connector substrate to the relay substrate, and the second actuator signal line has a larger outer diameter than an outer diameter of the first actuator signal line.

The above and other features, advantages and technical and industrial significance of this disclosure will be better understood by reading the following detailed description of presently preferred embodiments of the disclosure, when considered in connection with the accompanying drawings.

DETAILED DESCRIPTION

As modes for carrying out the present disclosure (hereinafter, referred to as "embodiments"), as endoscope system including an endoscope provided with an imager (imaging unit) in a distal end portion on a distal end side of an insertion portion that is inserted into a subject will be described below. The present disclosure is not limited by the embodiments below. Further, in description of the drawings, the same components are denoted by the same reference symbols. Furthermore, it is necessary to note that the drawings are schematic, and a relation between a thickness and a width of each of the components, ratios among the components, and the like are different from actual ones. Moreover, the drawings may include a portion that has different dimensional relations or ratios.

First Embodiment

Configuration of Endoscope System

Figure 1:
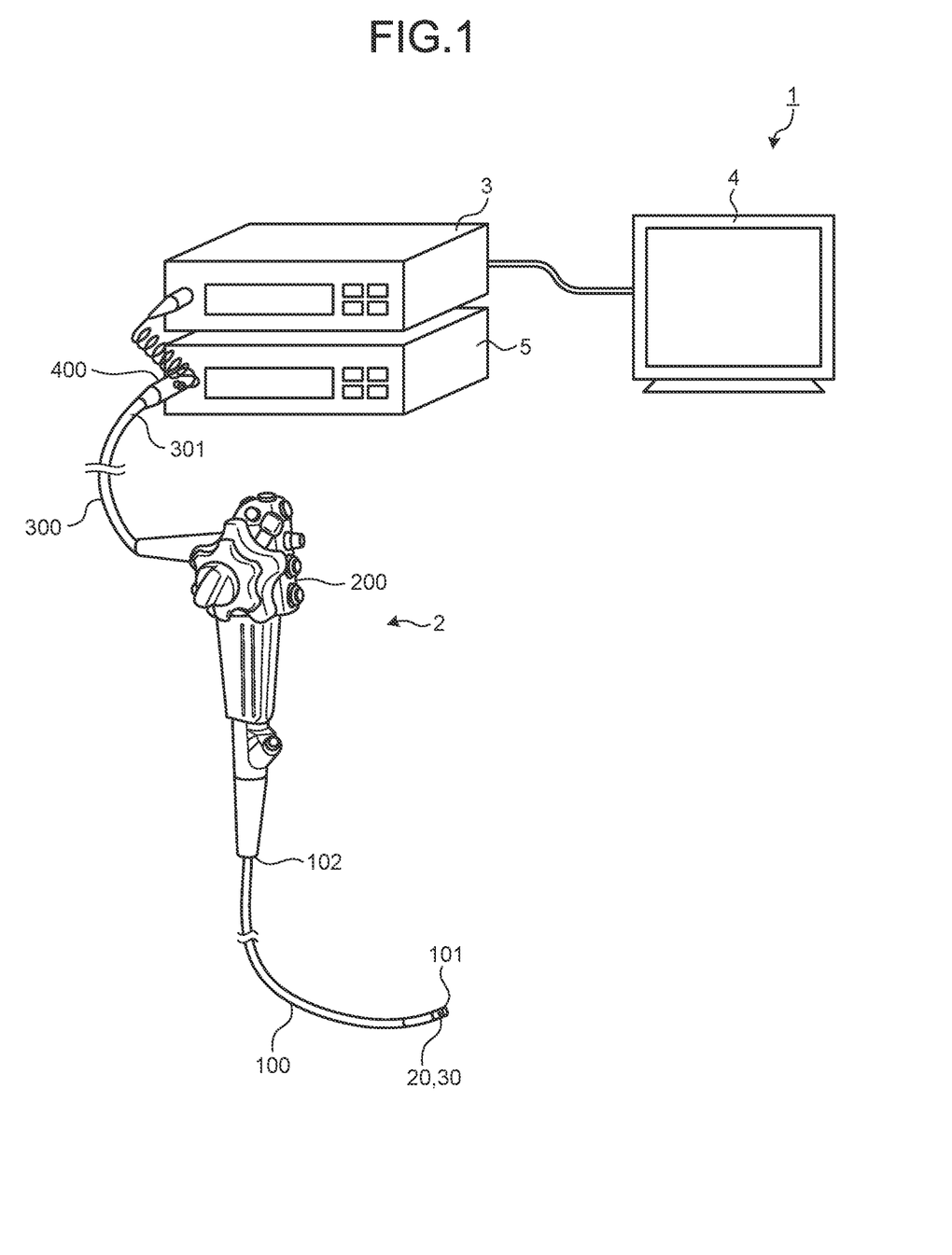
FIG. 1 is an overall diagram schematically illustrating an entire configuration of an endoscope system according to a first embodiment of the present disclosure.

FIG. 1 is an overall diagram schematically illustrating an entire configuration of an endoscope system according to a first embodiment of the present disclosure. An endoscope system 1 illustrated in FIG. 1 includes an endoscope 2, a processing device 3, a display device 4, and a light source device 5.

The endoscope 2 generates an imaging signal by inserting an insertion portion 100 including a plurality of cables into a body cavity of a subject and capturing an image of the inside of the subject, and outputs the generated imaging signal to the processing device 3. The endoscope 2 includes the insertion portion 100, an operating portion 200, a universal cord 300, and a proximal end portion 400.

The insertion portion 100 includes, inside thereof, a plurality of cables and a light guide, and is inserted into the body cavity of the subject. A distal end portion 101 to be inserted into the body cavity of the subject is connected to a distal end of the insertion portion 100. An imager 20 that generates an imaging signal by capturing an image of the inside of the subject and an actuator 30 are arranged in the distal end portion 101. The operating portion 200 is connected to a proximal end of the insertion portion 100. The insertion portion 100 transmits electric power and a driving signal supplied from the processing device 3 to the imager 20 and the actuator 30, and transmits the imaging signal generated by the imager 20 to the proximal end.

The operating portion 200 includes a built-in substrate in which various circuits are mounted, and receives input of various kinds of operation on the endoscope 2. Further, the operating portion 200 is connected to the universal cord 300.

The operating portion 200 is configured with various switches, a toggle switch, a button, and the like.

The universal cord 300 includes, inside thereof, a plurality of cables and a light guide, and includes a proximal end that is connected to the proximal end portion 400. The universal cord 300 transmits the electric power and the driving signal supplied from the processing device 3 to the insertion portion 100 via the proximal end portion 400 and the operating portion 200, and transmits the imaging signal generated by the imager 20 to a proximal end of the universal cord 300 via the insertion portion 100 and the operating portion 200.

The proximal end portion 400 is removably connected to the processing device 3 and the light source device 5. The proximal end portion 400 transmits the electric power and the driving signal supplied from the processing device 3 to the universal cord 300, and transmits the imaging signal that is input via the universal cord 300 to the processing device 3.

The processing device 3 outputs the electric power and the driving signal to the proximal end portion 400, and receives the imaging signal input from the proximal end portion 400. The processing device 3 performs predetermined image processing on the imaging signal, and outputs the processed imaging signal to the display device 4. The processing device 3 controls each of the units of the endoscope system 1. The processing device 3 is configured with, for example, a central processing unit (CPU), a graphics processing unit (CPU), a field programmable gate array (FPGA), a digital signal processing (DSP), various circuits, a volatile memory, a non-volatile memory, and the like.

The display device 4 displays an image corresponding to the imaging signal that is subjected to the image processing by the processing device 3. Further, the display device 4 displays various kinds of information on the endoscope system 1. The display device 4 is configured with liquid crystal, organic electro luminescence (EL), or the like.

The light source device 5 supplies illumination light for applying irradiation light from the distal end portion 101 side of the insertion portion to a subject (object) via the proximal end portion 400. The light source device 5 is configured with a halogen lamp, a white light emitting diode (LED) that emits white light, or the like. Meanwhile, in the first embodiment, a case will be described in which a simultaneous illumination method is adopted in the light source device 5, but it is possible to appropriately change the method in accordance with a type of the imager 20. For example, a frame sequential illumination method may be adopted.

Configurations of Endoscope and Processing Device

Figure 2:
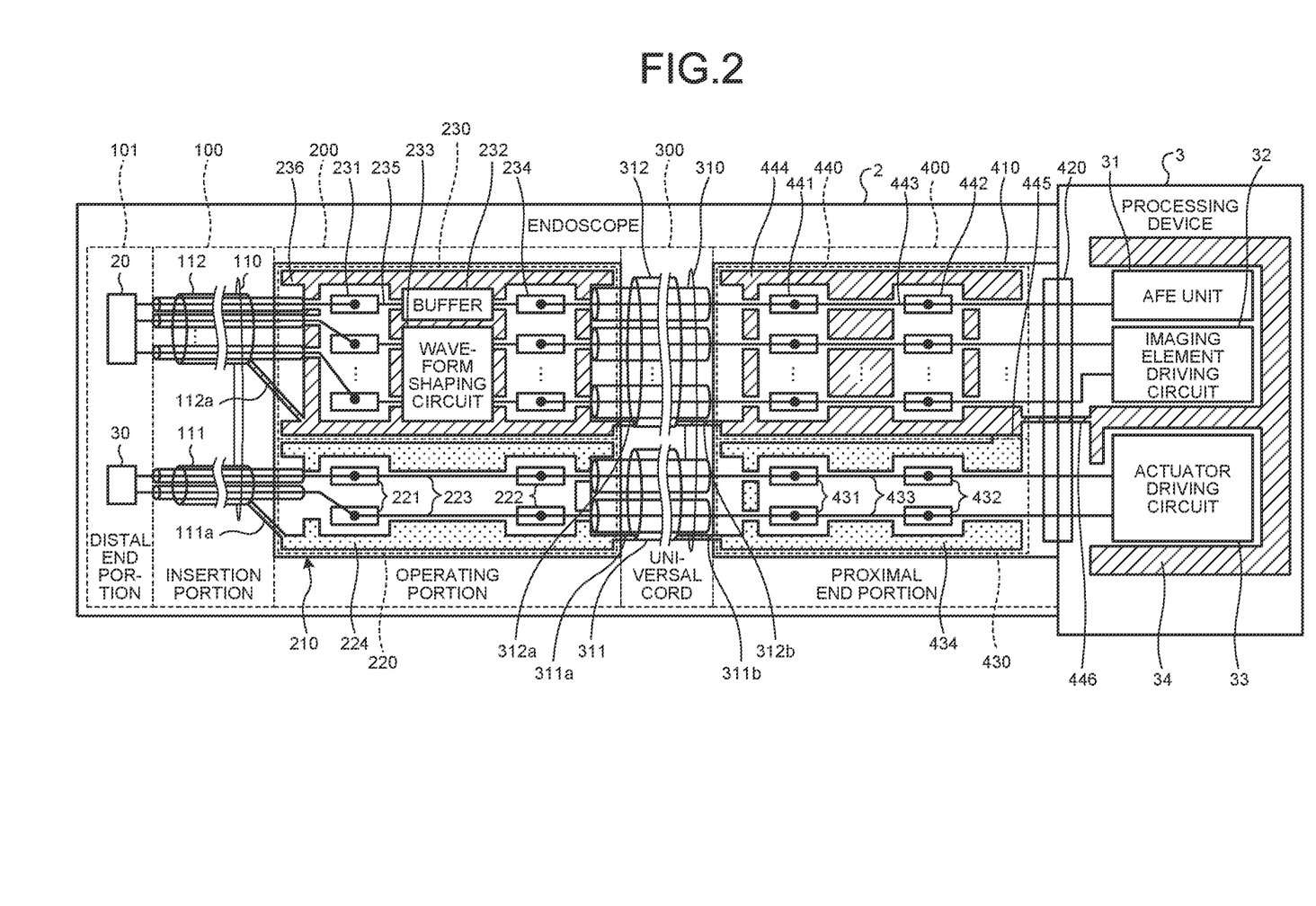
FIG. 2 is a schematic diagram illustrating configurations of an endoscope and a processing device according to the first embodiment of the present disclosure.

Detailed configurations of the endoscope 2 and the processing device 3 will be described below. FIG. 2 is a schematic diagram illustrating the configurations of the endoscope 2 and the processing device 3.

Configuration of Endoscope

First, the configuration of the endoscope 2 will be described.

As illustrated in FIG. 2, the endoscope 2 includes the distal end portion 101, the insertion portion 100, the operating portion 200, the universal cord 300, and the proximal end portion 400.

The distal end portion 101 includes the imager 20 (imaging unit) and the actuator 30.

The imager 20 includes an optical system that forms an object image on a light receiving surface of an imaging element, and the imaging element that generates an imaging signal by receiving light of the object image that is formed by the optical system and performing photoelectric conversion on the light. Among the components as described above, the optical system is configured with one or more lenses, is movable along an optical axis direction, and changes a focal distance by moving in the optical axis direction under the control of the actuator 30. Further, the imaging element sequentially generates imaging signals on the basis of a driving signal, a control signal, driving power, and the like that are transmitted through a first cable 110 arranged in the insertion portion 100 (to be described later), and outputs the generated imaging signals to the first cable 110. The imaging element is configured with, for example, a complementary metal oxide semiconductor (CMOS), a charge coupled device (CCD), or the like.

The actuator 30 is configured with a cylindrical magnetic body or the like, on which a coil and the optical system of the imager 20 are mounted. The actuator 30 generates magnetic field when the driving signal transmitted from the first cable 110 flows to the coil, and causes the magnetic body to move in the optical axis direction due to the magnetic field, thereby changing the focal distance of the optical system of the imager 20. Meanwhile, the actuator 30 may be configured with a voice coil motor, or may be configured with shape-memory alloy such that the shape is changed due to application of voltage.

The insertion portion 100 includes the first cable 110. The first cable 110 includes a first actuator signal line 111 and a first imaging signal line 112.

The first actuator signal line 111 is configured with a two-core shielded line and has an outer diameter of a first $\varphi 1$. One end side of the first actuator signal line 111 is electrically connected to the actuator 30, and the other end side of the first actuator signal line 111 is electrically connected to a relay substrate 210 of the operating portion 200 (to be described later). Further, a shielded line 111a of the first actuator signal line 111 is electrically connected to the relay substrate 210.

The first imaging signal line 112 is configured with a plurality of shielded lines (the sufficient number of lines for signals for driving the imager 20 and video output signals) and has an outer diameter of a second $\varphi 2$. One end side of the first imaging signal line 112 is electrically connected to the imager 20, and the other end side of the first imaging signal line 112 is electrically connected to the relay substrate 210. Further, a shielded line 112a of the first imaging signal line 112 is electrically connected to the relay substrate 210.

The operating portion 200 includes the relay substrate 210 to which the first cable 110 is electrically connected. The relay substrate 210 includes a first wiring portion 220 and a second wiring portion 230.

The first wiring unit 220 is electrically connected to the first actuator signal line 111 and the shielded line 111a. The first wiring portion 220 includes a plurality of distal end side connection lands 221, proximal end side connection lands 222, a plurality of signal lines 223, and a first ground plane 224.

The distal end side connection lands 221 are electrically connected to the other end side of the first actuator signal line 111 by solder or the like, and are electrically connected to the signal lines 223 by solder or the like. The plurality of signal lines 223 electrically connect the distal end side connection lands 221 and the proximal end side connection lands 222. The proximal end side connection lands 222 are electrically connected to a second actuator signal line 311 of the universal cord 300 (to be described later).

The first ground plane 224 is electrically connected to the shielded line 111a of the first actuator signal line 111, and is electrically connected to a shielded line 311*a* of the second actuator signal line 311 of the universal cord 300 (to be described later).

The second wiring portion 230 is electrical connected to the first imaging signal line 112 and the shielded line 112*a*. The second wiring portion 230 includes a plurality of distal end side connection lands 231, a buffer 232, a waveform shaping circuit 233, a plurality of proximal end side connection lands 234, signal lines 235, and a second ground plane 236.

The distal end side connection lands 231 are electrically connected to the other end side of the first imaging signal line 112, and are connected to the signal lines 235. The plurality of signal lines 235 are electrically connected to the proximal end side connection lands 234 via the buffer 232 or the waveform shaping circuit 233.

One end side of the buffer 232 is electrically connected to the distal end side connection land 231 via the signal line 235, and the other end side of the buffer 232 is electrically connected to the proximal end side connection land 234 via the signal line 235. The buffer 232 temporarily holds the imaging signal generated by the imager 20, amplifies the imaging signal, and outputs the amplified imaging signal to a second imaging signal line 312 of the universal cord 300 (to be described later). Meanwhile, in the first embodiment, the buffer 232 functions as a processing circuit.

One end side of the waveform shaping circuit 233 is electrically connected to the distal end side connection lands 231 via the signal lines 235, and the other end side of the waveform shaping circuit 233 is electrically connected to the proximal end side connection lands 234 via the signal lines 235. The waveform shaping circuit 233 performs waveform shaping on the driving signal, the control signal, and driving power that are input from the second imaging signal line 312 of the universal cord 300 (to be described later), and outputs them to the first imaging signal line 112.

One end side of the second ground plane 236 is electrically connected to the shielded line 112*a*, and the other end side of the second ground plane 236 is electrically connected to a shielded line 312*a* of the second imaging signal line 312 of the universal cord 300 (to be described later). Further, the second ground plane 236 and the first ground plane 224 are arranged so as to be spatially separated from each other on the same plane of the relay substrate 210.

The universal cord 300 includes at least a second cable 310. The second cable 310 includes the second actuator signal line 311 and the second imaging signal line 312.

The second actuator signal line 311 is configured with a two-core shielded line and has an outer diameter of the second φ2. Specifically, the second actuator signal line 311 has a larger outer diameter than the outer diameter of the first actuator signal line 111 (first φ1<second φ2). One end of the second actuator signal line 311 is electrically connected to the proximal end side connection lands 222 of the first wiring portion 220, and the other end side of the second actuator signal line 311 is connected to the proximal end portion 400 (to be described later). Further, one end side of the shielded line 311*a* of the second actuator signal line 311 is electrically connected to the first ground plane 224, and the other end side of the shielded line 311*a* of the second actuator signal line 311 is connected to the proximal end portion 400.

The second imaging signal line 312 is configured with a plurality of core shielded lines (the sufficient number of lines for signals for driving the imager 20 and video output signals). The second imaging signal line 312 has an outer diameter of a fourth φ4. The second imaging signal line 312 has a larger outer diameter than the outer diameter of the first imaging signal line 112 (second φ2<fourth φ4). One end side of the second imaging signal line 312 is electrically connected to the proximal end side connection lands 234 of the second wring portion 230, and the other end side of the second imaging signal line 312 is electrically connected to the proximal end portion 400. Further, one end side of the shielded line 312*a* of the second imaging signal line 312 is electrically connected to the second ground plane 236, and the other end side of the shielded line 312*a* of the second imaging signal line 312 is connected to the proximal end portion 400.

The proximal end portion 400 includes a connector substrate 410 to which the second cable 310 is electrically connected, and a connector 420 that is removably and electrically connected to the processing device 3. Further, the connector substrate 410 includes a third wiring portion 430 and a fourth wiring portion 440.

The third wiring portion 430 is electrically connected to the second actuator signal line 311 and the shielded line 311*a*. The third wiring portion 430 includes a plurality of distal end side connection lands 431, a plurality of proximal end side connection lands 432, a plurality of signal lines 433, and a third ground plane 434. One end side of the distal end side connection lands 431 is electrically connected to the second actuator signal line 311, and the distal end side connection lands 431 is electrically connected to the signal lines 433. The plurality of signal lines 433 electrically connect the distal end side connection lands 431 and the proximal end side connection lands 432. The proximal end side connection lands 432 are electrically connected to the connector 420 via the signal lines 433. Further, the third ground plane 434 is electrically connected to the shielded line 311*a* of the second actuator signal line 311.

The fourth wiring portion 440 is electrically connected to the second imaging signal line 312 and the shielded line 312*a*. The fourth wiring portion 440 includes a plurality of distal end side connection lands 441, a plurality of proximal end side connection lands 442, a plurality of signal lines 443, and a fourth ground plane 444. The distal end side connection lands 441 are electrically connected to the second imaging signal line 312, and are electrically connected to the signal lines 443. The plurality of signal lines 443 electrically connect the distal end side connection lands 441 and the proximal end side connection lands 442. The proximal end side connection lands 442 are electrically connected to the connector 420 via the signal lines 443. The fourth ground plane 444 includes a connection portion 445 that is electrically connected to the third ground plane 434 on the same plane of the connector substrate 410. Further, the fourth ground plane 444 includes a wire 446 that is electrically connected to the connector 420. The fourth ground plane 444 is electrically connected, via the connector 420, to a common ground plane 34 arranged on the processing device 3 (to be described later).

One end side of the connector 420 is electrically connected to the proximal end side connection lands 432 via the signal lines 433, and the connector 420 is electrically connected to the proximal end side connection lands 442 via the signal lines 443. Further, the connector 420 is electrically connected to the wire 446 of the fourth ground plane 444. The connector 420 is removably connected to the processing device 3, and is electrically connected to various circuits and the common ground plane 34 of the processing device 3 (to be described later).

Configuration of Processing Device

The configuration of the processing device 3 will be described below.

The processing device 3 includes an analog front end 31 (hereinafter, described as the "AFE 31"), an imaging element driving circuit 32, an actuator driving circuit 33, and the common ground plane 34.

The AFE 31 performs predetermined signal processing, such as an analog-to-digital conversion process and a denoising process, on the imaging signal that has been input via the second imaging signal line 312 and the connector 420, and outputs the imaging signal to an image processing engine (not illustrated).

The imaging element driving circuit 32 generates a driving signal, a control signal, and driving power for driving the imager 20, and outputs the driving signal, the control signal, and the driving power to the second imaging signal line 312 via the connector 420.

The actuator driving circuit 33 generates a driving signal for driving the actuator 30, and outputs the generated driving signal to the second actuator signal line 311 via the connector 420.

The common ground plane 34 is electrically connected to the fourth ground plane 444 via the connector 420 and the wire 446.

According to the first embodiment as described above, the first ground plane 224 and the second ground plane 236 are arranged in a separated manner on the relay, substrate 210, and the second actuator signal line 311 has a larger outer diameter than the outer diameter of the first actuator signal line 111, so that it is possible to reduce the size of the driving circuit and prevent noise generated from the driving circuit for driving the actuator 30 from being superimposed on the imaging signal. As a result, it is possible to improve observation performance.

Furthermore, according to the first embodiment, the connector substrate 410 and the relay substrate 210 are electrically connected by the second actuator signal line 311 having a low resistance value, and the relay substrate 210 and the actuator 30 are electrically connected by the first actuator signal line 111, so that it is possible to reduce synthetic impedance of the signal line for the actuator 30, and it is possible to reduce driving voltage of the actuator driving circuit 33 of the processing device 3.

Second Embodiment

A second embodiment will be described below. An endoscope according to the second embodiment has a different configuration from the endoscope 2 according to the first embodiment as described above. Specifically, in the first embodiment, the first ground plane 224 and the second ground plane 236 are arranged in a spatially separated manner on the same plane of the relay substrate 210; however, in the second embodiment, the first ground plane and the second ground plane are arranged on different planes. In the following, a configuration of the endoscope according to the second embodiment will be described. Meanwhile, the same components as those of the endoscope system 1 according to the first embodiment as described above are denoted by the same reference symbols, and detailed explanation thereof will be omitted.

Configuration of Endoscope

Figure 3:
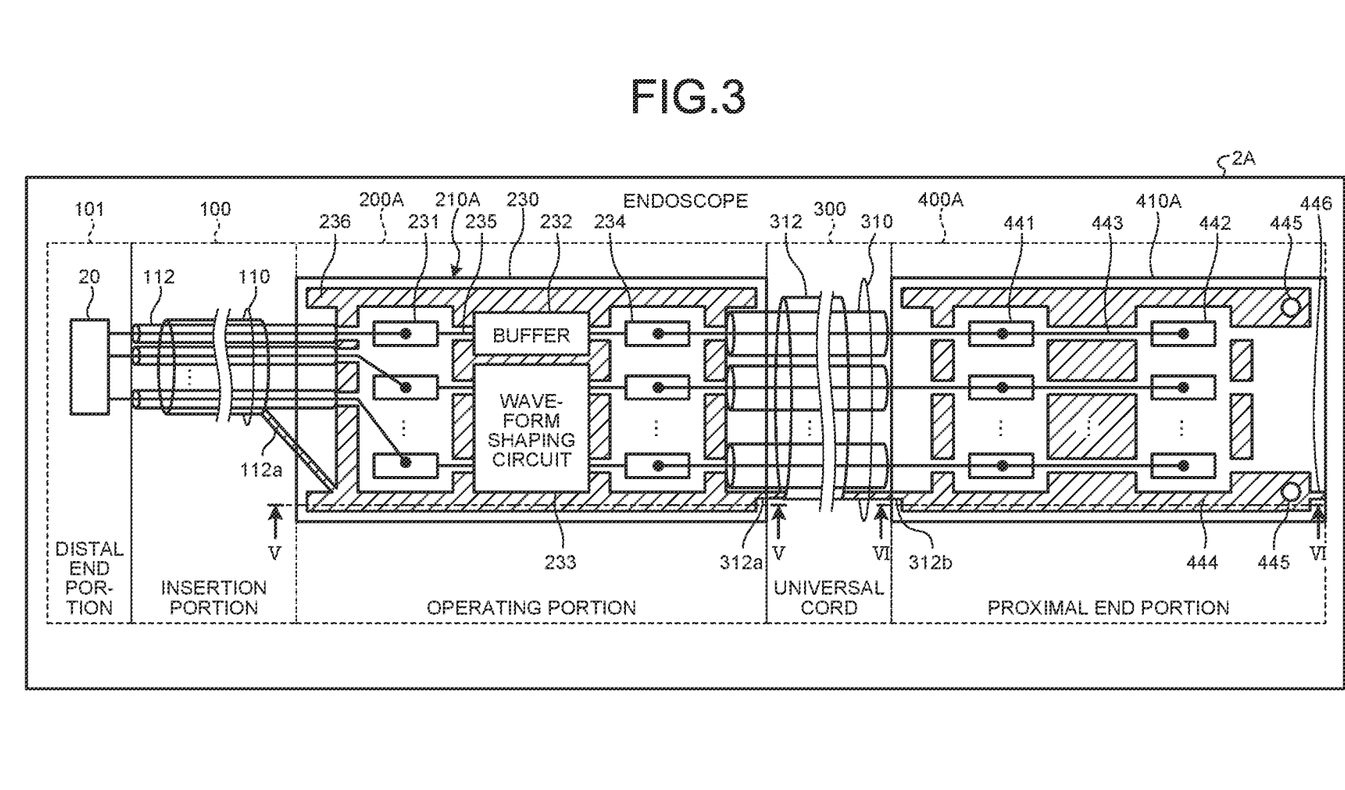
FIG. 3 is a schematic diagram illustrating a configuration of a front surface side of the endoscope according to a second embodiment of the present disclosure.
Figure 4:
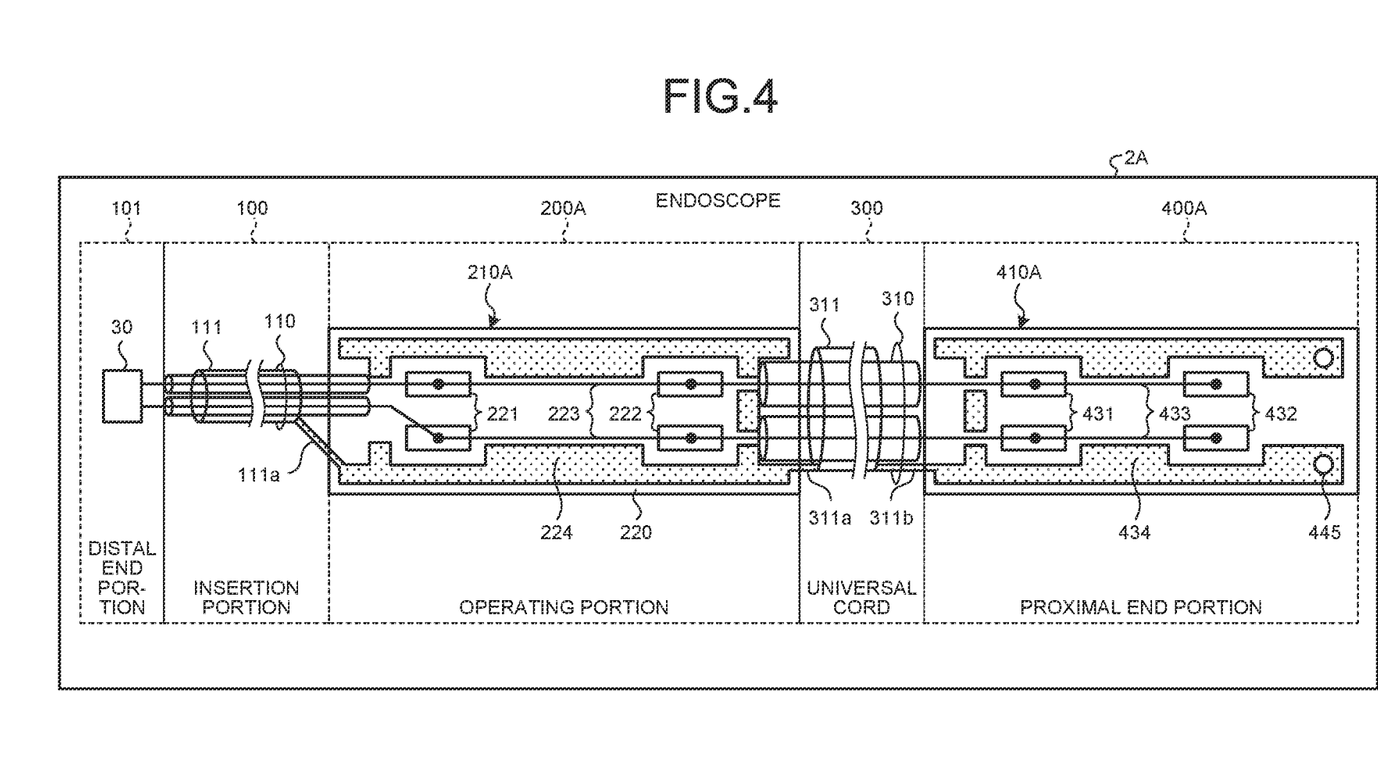
FIG. 4 is a schematic diagram illustrating a configuration of a back surface side of the endoscope according to the second embodiment of the present disclosure.
Figure 5:
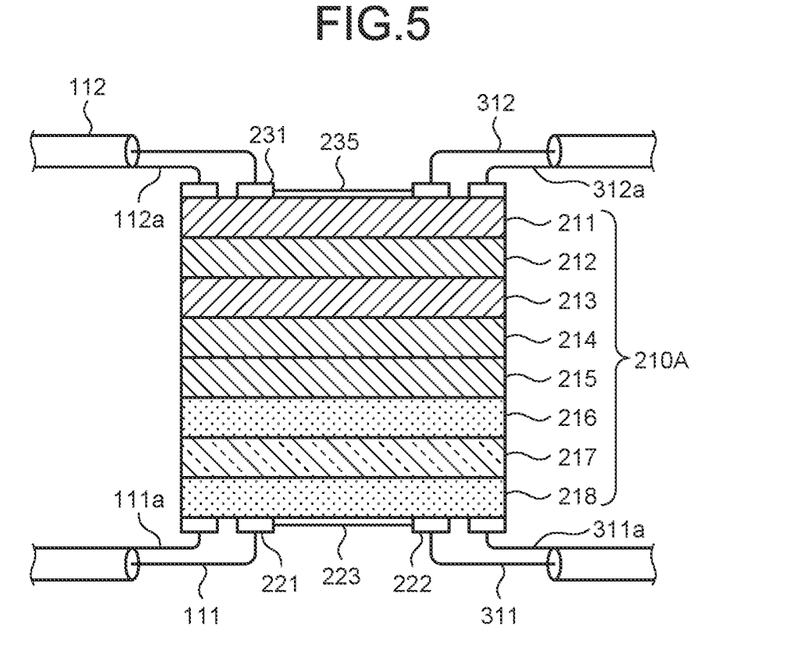
FIG. 5 is a cross-sectional view taken along a line V-V illustrated in FIG. 3.
Figure 6:
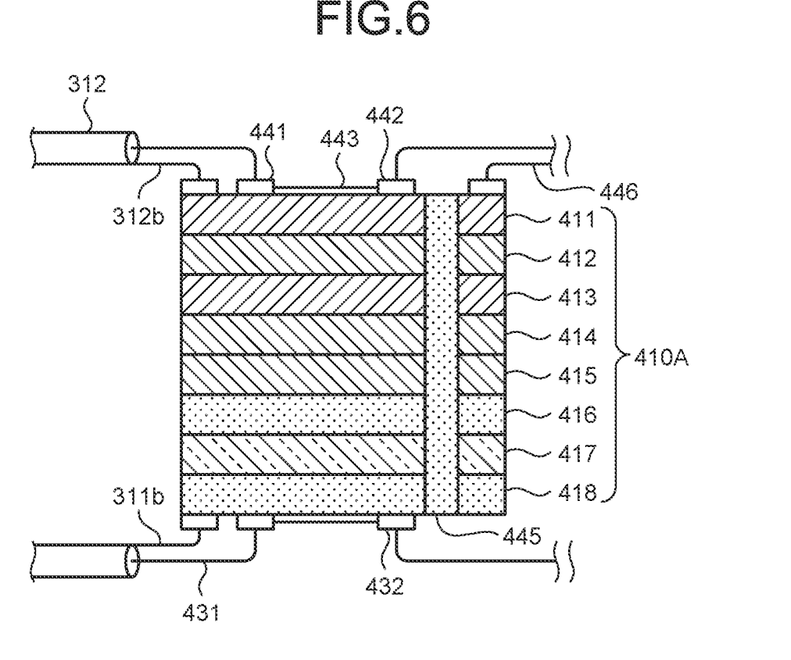
FIG. 6 is a cross-sectional view taken along a line VI-VI illustrated in FIG. 3.

FIG. 3 is a schematic diagram illustrating a configuration of a front surface side of the endoscope. FIG. 4 is a schematic diagram illustrating a configuration of a back surface side of the endoscope. FIG. 5 is a cross-sectional view taken along a line V-V illustrated in FIG. 3. FIG. 6 is a cross-sectional view taken along a line VI-VI illustrated in FIG. 3.

An endoscope 2A illustrated in FIG. 3 to FIG. 6 includes an operating portion 200A and a proximal end portion 400A instead of the operating portion 200 and the proximal end portion 400 of the endoscope 2 according to the first embodiment as described above. The operating portion 200A and the proximal end portion 400 respectively include a relay substrate 210A and a connector substrate 410A instead of the relay substrate 210 and the connector substrate 410 of the first embodiment as described above. The relay substrate 210A and the connector substrate 410A illustrated in FIG. 3 to FIG. 6 are configured with eight-layer substrates, in which an imaging signal cable (the first imaging signal line 112 and the second imaging signal line 312) and an imaging signal ground (the second ground plane 236 and the fourth ground plane 444) are arranged on the front surface side, and an actuator signal cable (the first actuator signal line 111 and the second actuator signal line 311) and an actuator signal ground (the first ground plane 224 and the third ground plane 434) are arranged on a back surface side.

The relay substrate 210A is formed of a first layer 211, a second layer 212, a third layer 213, a fourth layer 214, a fifth layer 215, a sixth layer 216, a seventh layer 217, and an eighth layer 218 in this order from the front surface side to the back surface side.

The second ground plane 236, the buffer 232, and the waveform shaping circuit 233 are arranged on the first layer 211. The second ground plane 236 is electrically connected to the third layer 213 that functions as a ground layer for the imager 20, by a penetration via or a through silicon via (TSV) (not illustrated). On the second layer 212, a circuit or a capacity for wiring the buffer 232, the waveform shaping circuit 233, and the like is formed, for example. The fourth layer 214 and the fifth layer 215 function as power supply layers for the imaging signal.

The sixth layer 216 functions as a ground layer for the actuator 30. The seventh layer 217 functions as a signal layer for the actuator 30. On the eighth layer 218, the distal end side connection lands 221, the proximal end side connection lands 222, and the first ground plane 224 are arranged. The first ground plane 224 is electrically connected to the sixth layer 216 by a penetration via or a TSV (not illustrated). Further, the first ground plane 224 and the second ground plane 236 are laminated such that they are insulated between the layers.

The connector substrate 410A is formed of a first layer 411, a second layer 412, a third layer 413, a fourth layer 414, a fifth layer 415, a sixth layer 416, a seventh layer 417, and an eighth layer 416 in this order from the front surface side to the back surface side.

The distal end side connection lands 441, the proximal end side connection lands 442, and the fourth ground plane 444 are arranged on the first layer 411. The fourth ground plane 444 is electrically connected to the third layer 413 that functions as a ground layer for the imager 20, by a penetration via or a TSV (not illustrated). On the second layer 412, a circuit or a capacity is formed. The fourth layer 414 and the fifth layer 415 function as power supply layers for the imaging signal.

The sixth layer 416 functions as a ground layer for the actuator 30. The seventh layer 417 functions as a signal layer for the actuator 30. On the eighth layer 418, the distal end side connection lands 431, the proximal end side connection lands 432, and the third ground plane 434 are arranged. The third ground plane 434 is electrically connected to the fourth ground plane 444 via penetration vias 445.

According to the second embodiment as described above, the relay substrate 210A and the connector substrate 410A are configured as laminated structures, so that it is possible to reduce planar areas of the relay substrate 210A and the connector substrate 410A, reduce a size of the operating portion 200A, and reduce assembly cost of the endoscope 2A.

Furthermore, according to the second embodiment, in the relay substrate 210A and the connector substrate 410A, the second layers 212 and 412, the fourth layers 214 and 414, the fifth layers 215 and 415, and the seventh layers 217 and 417 are sandwiched between upper and lower ground plane layers for transmitting imaging driving signals and actuator driving signals, so that it is possible to prevent noise from being radiated to outside.

Third Embodiment

A third embodiment will be described below. In the first embodiment as described above, the signal lines are electrically connected to the connection lands by solder or the like, and the first cable of the insertion portion and the second actuator signal line of the universal cord have different outer diameters; however, in the third embodiment, electrical connection is established using a coaxial connector, and the first actuator signal line and the second actuator signal line have the same outer diameters. In the following, a configuration of an endoscope according to the third embodiment will be described. Meanwhile, the same components as those of the endoscope system 1 according to the first embodiment as described above are denoted by the same reference symbols, and detailed explanation thereof will be omitted.

Configuration of Endoscope

Figure 7:
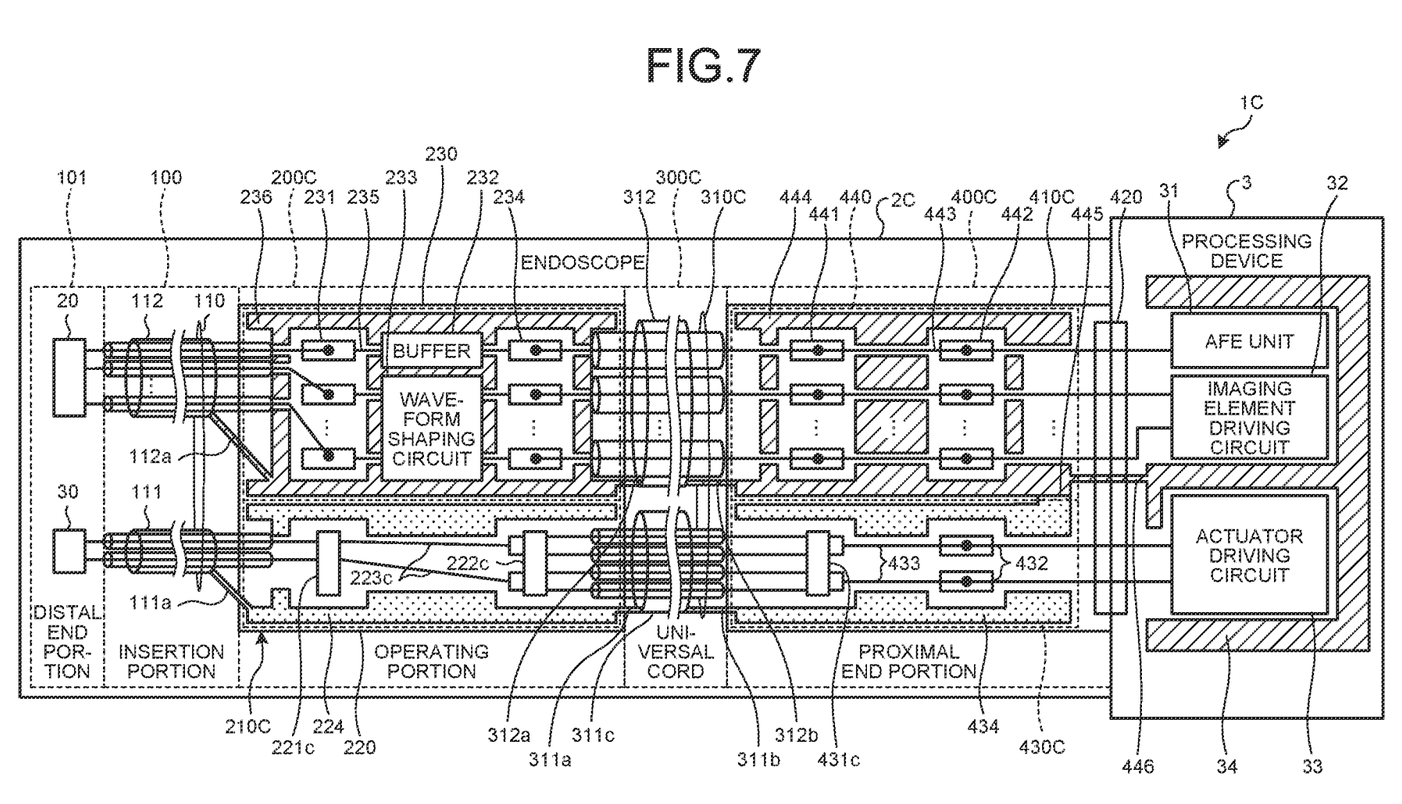
FIG. 7 is a schematic diagram illustrating a configuration of an endoscope according to a third embodiment of the present disclosure.

FIG. 7 is a schematic diagram illustrating a configuration of an endoscope according to the third embodiment. An endoscope 2C illustrated in FIG. 7 includes an operating portion 200C, a universal cord 300C, and a proximal end portion 400C instead of the operating portion 200, the universal cord 300, and the proximal end portion 400 of the endoscope 2 according to the first embodiment as described above. The operating portion 200C, the universal cord 300C, and the proximal end portion 400C respectively include a relay substrate 210C, a second cable 310C, and a connector substrate 410C instead of the relay substrate 210, the second cable 310, and the connector substrate 410 according to the first embodiment as described above.

The relay substrate 210C includes the first wiring portion 220 and the second wiring portion 230. The first wiring portion 220 includes a distal end side connection land 221c, a thin-line coaxial connector 222c, a plurality of signal lines 223c, and the first ground plane 224.

The distal end side connection land 221c is electrically connected to the other end side of the first actuator signal line 111 and the plurality of signal lines 223c. The plurality of signal lines 223c electrically connect the distal end side connection land 221c and the thin-line coaxial connector 222c. The thin-line coaxial connector 222c is electrically removably connected to a second actuator signal line 311c of the universal cord 300C (to be described below).

The second cable 310C includes the second actuator signal line 311c and the second imaging signal line 312. The second actuator signal line 311c is configured with a four-core shielded line, and configured by arranging, side by side, two-core shielded lines that are the same as that of the first actuator signal line 111 as described above. Accordingly, it is possible to reduce the resistance value of the second actuator signal line 311c by half of that of the second actuator signal line 311 of the first embodiment as described above. Further, one end side of the second actuator signal line 311c is electrically removably connected to the thin-line coaxial connector 222c, and the other end side of the second actuator signal line 311c is electrically removably connected to a thin-line coaxial connector 431c of the connector substrate 410C.

The connector substrate 410C includes a third wiring portion 430c and the fourth wiring portion 440. The third wiring portion 430c is electrically connected to the second actuator signal line 311c and the shielded line 311a. The third wiring portion 430c includes the thin-line coaxial connector 431c, the plurality of proximal end side connection lands 432, the plurality of signal lines 433, and the third ground plane 434. One end of the thin-line coaxial connector 431c is electrically removably connected to the second actuator signal line 311c and the thin-line coaxial connector 431c is electrically connected to the signal line 433.

According to the third embodiment as described above, the second actuator signal line 311c is removably connected using the thin-line coaxial connector 222c and the thin-line coaxial connector 431c, so that it is possible to commonalize components, reduce cost at the time of assembly of the endoscope 2C, reduce component cost, and improve modifiability.

Meanwhile, in the third embodiment, the second actuator signal line 311c is configured using the two-core shielded lines that are the same as that of the first actuator signal line 111, but embodiments are not limited to this example, and it may be possible to use, as the second imaging signal line 312, a cable with the same diameter as that of the second actuator signal line 311c. Accordingly, it is possible to connect the imaging cable by a common thin-line coaxial connector, so that it is possible to further reduce assembly cost of the endoscope 2C, reduce component cost, and improve modifiability.

Other Embodiments

Various embodiments may be made by appropriately combining a plurality of constituent elements disclosed in the first to the third embodiments of the present disclosure as described above. For example, some constituent elements may be deleted from all of the constituent elements described in the first to the third embodiments of the present disclosure as described above. Furthermore, the constituent elements described in the first to the third embodiments of the present disclosure as described above may be appropriately combined.

Moreover, in the first to the third embodiments of the present disclosure, the control device and the light source device are separated, but they may be configured in an integrated manner.

Furthermore, in the first to the third embodiments of the present disclosure, the endoscope system is adopted, but it may be possible to adopt a video microscope that captures an image of a subject.

Moreover, in the first to the third embodiments of the present disclosure, the endoscope system including the flexible endoscope is described, but it may be possible to adopt an endoscope system including a rigid endoscope and an endoscope system including an industry endoscope.

Furthermore, in the first to the third embodiments of the present disclosure, the endoscope system including an endoscope that is inserted into a subject is described, but it may be possible to adopt, for example, an endoscope system including a rigid endoscope or an endoscope system including a nasal endoscope and an electric scalpel, an inspection probe, or the like.

Moreover, in the first to the third embodiments of the present disclosure, the "unit" described above may be replaced with a "means", a "circuit", or the like. For example, the control unit may be replaced with a control means or a control circuit.

According to the present disclosure, it is possible to reduce a size of a driving circuit, and prevent noise from being superimposed on an imaging signal.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an insertion portion to be inserted into a subject;
   a distal end portion that is arranged on a distal end side of the insertion portion, the distal end portion including an imager and an actuator, the imager being configured to adjust a focal point and generate an imaging signal by capturing an image of an object, the actuator being configured to adjust a focal point of the imager based on a driving signal that is input from outside;
   an operating portion that is arranged on a proximal end side of the insertion portion, the operating portion including a relay substrate that is electrically connected to the imager and the actuator via a first cable;
   a connector substrate that is electrically connected to the relay substrate via a second cable; and
   a proximal end portion including a connector configured to receive input of the driving signal from a processing device and output the imaging signal to the processing device, wherein
   the first cable includes a first actuator signal line that transmits the driving signal from the relay substrate to the actuator,
   the second cable includes a second actuator signal line that transmits the driving signal from the connector substrate to the relay substrate, and
   the second actuator signal line has a larger outer diameter than an outer diameter of the first actuator signal line.

2. The endoscope according to claim 1, wherein
   the relay substrate includes a first wiring portion and a second wiring portion,
   the first wiring portion includes a first ground plane to which a shielded line of the first actuator signal line and a shielded line of the second actuator signal line are electrically connected,
   the first wiring portion is configured to electrically connect the first actuator signal line and the second actuator signal line,
   the second wiring portion includes a second ground plane and a processing circuit configured to perform processing on the imaging signal, and
   the first ground plane and the second ground plane are arranged in a separated manner on the relay substrate.

3. The endoscope according to claim 2, wherein
   the first cable further includes a first imaging signal line that transmits the imaging signal from the imager to the processing circuit,
   the second cable further includes a second imaging signal line that transmits the imaging signal from the processing circuit to the connector,
   a shielded line of the first imaging signal line and a shielded line of the second imaging signal line are electrically connected to the second ground plane,
   the connector substrate includes a third wiring portion and a fourth wiring portion,
   the third wiring portion includes a third ground plane to which a shielded line of the second actuator signal line is connected,
   the third wiring portion is electrically connected to the second actuator signal line,
   the fourth wiring portion includes a fourth ground plane to which the shielded line of the second imaging signal line is connected,
   the fourth wiring portion is electrically connected to the second imaging single line,
   the third ground plane and the fourth ground plane are electrically connected to each other.

4. The endoscope according to claim 2, wherein the first ground plane and the second ground plane are arranged in a spatially separated manner on a same plane of the relay substrate.

5. The endoscope according to claim 2, wherein
   the first wiring portion is arranged on a back surface of the relay substrate, and
   the second wiring portion is arranged on a front surface of the relay substrate.

6. The endoscope according to claim 3, wherein the third ground plane and the fourth ground plane are connected to each other on a same plane of the connector substrate.

7. The endoscope according to claim 3, wherein
   the third wiring portion is arranged on a back surface of the connector substrate,
   the fourth wiring portion is arranged on a front surface of the connector substrate, and
   the third ground plane and the fourth ground plane are electrically connected to each other by a penetration via.

* * * * *